(12) United States Patent
Fitzsimmons (10) Patent No.: US 6,364,824 B1
(45) Date of Patent: Apr. 2, 2002

(54) STIMULATING CELL RECEPTOR ACTIVITY USING ELECTROMAGNETIC FIELDS

(75) Inventor: Robert J. Fitzsimmons, Mentone, CA (US)

(73) Assignee: Orthofix, Inc., Richardson, TX (US)

( * ) Notice: Subject to any disclaimer, the term of this patent is extended or adjusted under 35 U.S.C. 154(b) by 0 days.

(21) Appl. No.: 09/438,749

(22) Filed: Nov. 11, 1999

Related U.S. Application Data (60) Provisional application No. 60/107,927, filed on Nov. 11, 1998.

(51) Int. Cl.[7] .................................................. A61N 2/02
(52) U.S. Cl. ........................................... 600/13; 600/15
(58) Field of Search ............................... 600/9, 10, 13, 600/14, 15

(56) References Cited

U.S. PATENT DOCUMENTS

| | | | |
|---|---|---|---|
| 3,915,151 A | | 10/1975 | Kraus |
| 4,266,532 A | * | 5/1981 | Ryaby et al. ................. 600/14 |
| 4,993,413 A | | 2/1991 | McLeon |
| 5,014,699 A | | 5/1991 | Pollack |
| 5,156,587 A | | 10/1992 | Montone |
| 5,267,939 A | | 12/1993 | Liboff |
| 5,318,561 A | | 6/1994 | McLeod |
| 5,413,596 A | | 5/1995 | Kronberg |
| 5,458,558 A | | 10/1995 | Liboff |
| 5,743,844 A | | 4/1998 | Tepper |
| 5,792,209 A | | 8/1998 | Varner |
| 5,997,464 A | | 12/1999 | Blackwell |
| 6,004,257 A | * | 12/1999 | Jacobson ........................ 600/9 |
| 6,024,691 A | * | 2/2000 | Tepper et al. ................. 600/13 |

FOREIGN PATENT DOCUMENTS

| | | |
|---|---|---|
| WO | WO 90/07356 | 7/1990 |

* cited by examiner

*Primary Examiner*—John P. Lacyk
*Assistant Examiner*—Joseph A Cadugan
(74) *Attorney, Agent, or Firm*—John G. Flaim; William D. McSpadden; Baker & McKenzie (57) ABSTRACT

A method and associated apparatus are presented for stimulating biological activity of cell receptors. The biological activity of cell receptors is stimulated by positioning a transmitter in proximity with the target cell receptors, generating an electromagnetic field, such that the flux of the electromagnetic field extends through the target cell receptors, and fluctuating the electromagnetic field at a predetermined rate of fluctuation. An associated apparatus is presented which stimulates biological activity of cell receptors. The apparatus comprises a field coil electrically connected to an alternating current source with a predetermined rate of fluctuation. The alternating current flows through the field coils, thereby generating an electromagnetic field with a predetermined rate of fluctuation.

8 Claims, 5 Drawing Sheets

FIG. 5

- POSITIONING A TRANSMITTER IN PROXIMITY TO ONE OR MORE CELL RECEPTOR(s) — 505
- GENERATING AN ELECTROMAGNETIC FIELD SUCH THAT THE FLUX OF THE ELECTROMAGNETIC FIELD EXTENDS THROUGH THE TARGET RECEPTOR — 510
- FLUCTUATING ELECTROMAGNETIC FIELD AT A PREDETERMINED RATE — 515
- END

STIMULATING CELL RECEPTOR ACTIVITY USING ELECTROMAGNETIC FIELDS

CLAIM OF PRIORITY

The instant patent application claims priority from the U.S. provisional patent application designated with serial No. 60/107,927, entitled "Method, Device, and System for Increasing the Number of Bone Cells Using and Electromagnetic Field(s)", filed on Nov. 11, 1998.

TECHNICAL FIELD

The present invention relates to stimulating cell receptor activity, and more particularly, to using electromagnetic fields to stimulate cell receptor activity.

BACKGROUND

Osteoporosis is a disease characterized by a decrease in bone mass which leads to spontaneous bone fractures or a bone fracture occurring due to an impact that under normal conditions would not produce a bone fracture. The goal for treating osteoporosis is to build bone strength to a level sufficient to withstand normal loading conditions without failure.

A significant determinant of bone strength is bone mass. Bone mass is determined by the balance between the activity of osteoclast, which destroy bone, and osteoblast, which build bone. During homeostasis, in which bone mass is maintained at a constant level, the activity of the osteoclast and osteoblast are equal. The amount of bone being turned over by the activity of bone cells is 5–10% per year.

At approximately age 30 peak bone mass is achieved. At this stage the activity of osteoblasts begin to lag behind the activity of osteoclasts. This results in a loss of bone. The rate of bone loss varies between individuals but is generally greater in women when expressed as a percent of total bone compared to men. Furthermore, the drop in estrogen levels at menopause is accompanied by an increase in osteoclast activity. Estrogen is believed to act as a brake on osteoclast activity. The activity of osteoblast also increases but not to the same extent as the increase in osteoclast activity. The result is an even greater rate in the loss of bone compared with the pre-menopausal rate.

The health impact of osteoporosis includes loss of the quality of life as osteoporotic bone fractures usually occur in the elder who have a diminished healing capacity. Furthermore, approximately 20% of elderly women who suffer from an osteoporotic hip fracture will die within the next year. The health care cost due to osteoporosis is between 5 and 10 billion dollars per year in the United States.

Treatment of osteoporosis has focused on two fronts. One is inhibition of ostecclast to prevent further resorption of bone and the second is to stimulate osteoblast to form new bone. Osteoporosis therapies targeted at preventing bone resorption, include Hormone Replacement Therapy (HRT) which replaces the lost estrogen with therapeutic estrogen. However, side effects of HRT such as increased rate of breast cancer or cervical cancer has fueled the search for a better means of decreasing bone resorption. Currently, the most popular method of reducing bone resorption is through bisphosphonate based drugs. Fosamax from Merck is the leading market contender in this class of anti-bone resorbing drugs. Another therapeutic is calcitonin which is a naturally occurring protein that inhibits osteoclast activity and is now available as a nasal spray thereby eliminating the need for injections.

The second focus for osteoporosis therapy is to stimulate osteoblast to form more bone. Clinical studies conducted using osteoporotic patients indicate that the predominant determinant of bone formation was the number of osteoblast. Fluoride (NaF) therapy fits into this category as evidence indicates that bone formation is increased with NaF treatment However, there is also evidence that increased bone mass following NaF treatment does not translate to stronger bones as the quality of bone is compromised.

A general paradigm in biology is that mature, fully differentiated cells do not divide. Therefore, to increase the number of bone producing, fully differentiated bone cells it is necessary to first increase the number of pre-osteoblast cells and then induce their maturation into fully differentiated bone cells. Two factors which occur naturally in the body are insulin-like growth factor I (IGF-I) and transforming growth factor beta (TGFB). IGF-I and TGFB are in a class of proteins known as ligands. Using isolated bone cells in culture it can be demonstrated that IGF-I acts to increase the rate of proliferation of bone cells and TGFB acts to increase the differentiation state of bone cells.

The primary function of a ligand such as IGF-I or TGFB is to activate specific receptors located on the surface of cells. IGF-I activates the IGF-I receptor and TGFB activates the TGFB receptor. As such, alternative means of activating these receptors will result in the same biological endpoints as activation by the natural ligand. A technique that has been the subject of study is the use of an electromagnetic field (also referred to as a magnetic field) to activate receptors.

An early attempt at a receptor specific electromagnetic field theory was based on the assumption that the majority of binding energy in the ligand-receptor interaction was used for specificity. For a specific ligand to find a specific receptor while millions of other molecules are present a considerable loss of entropy (randomness) and, therefore, energy is required. Assumptions were made about the strength of the chemical bonds and the cost for overcoming entropy was subtracted to yield an amount of energy. This amount of energy was hypothesized to represent the amount of energy being used by the receptor to become activated. If this receptor 'activation' energy were unique for a particular receptor then it would be possible to apply an electromagnetic field that would impact the required energy to a receptor and activate it. However, the electromagnetic field energy that would be required to activate a receptor from these calculations was high and thermal heating of the water surrounding a cell would interfere with any specificity. Therefore, this technique is not preferable.

Accordingly, it would be advantageous to provide a technique to stimulate cell receptor activity with lower energy electromagnetic fields.

SUMMARY

This application discloses a method and apparatus for stimulating cell receptor activity for treatment of maladies such as osteoporosis. An electromagnetic field or signal is generated by a device positioned in proximity to one or more target cell receptors, such that the flux of the electromagnetic field extends through the target receptor. The electromagnetic field is then fluctuated at a predetermined rate.

The device comprises a transmitter for generating an electromagnetic field having a predetermined rate of fluctuation and a positioning apparatus for positioning the transmitter such that the flux of the electromagnetic field extends through the target receptor.

BRIEF DESCRIPTION OF THE DRAWINGS

The following detailed description of preferred embodiments refers to the accompanying drawings, in which.

DETAILED DESCRIPTION OF PREFERRED EMBODIMENTS

Figures 1, 2:
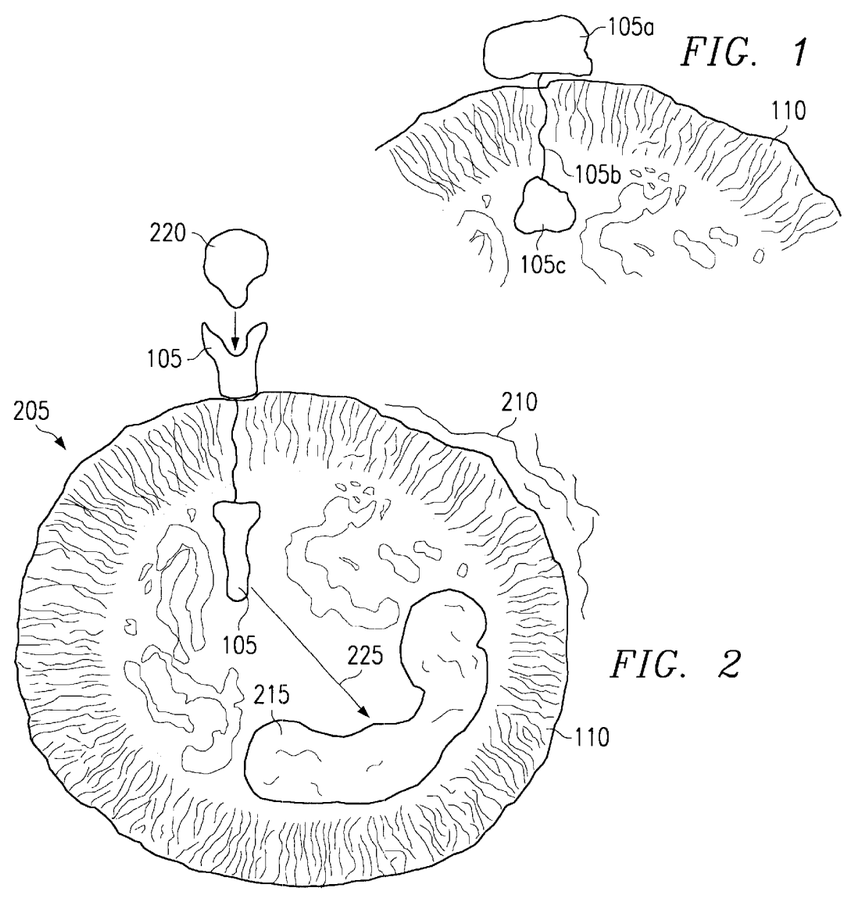
FIG. 1 is illustrated a block diagram of a cell receptor spanning a cell membrane.
FIG. 2 is a block diagram of a cellular environment.

Referring now to FIG. 1, there is illustrated a block diagram of a cell receptor 105 spanning a cell membrane 110. The cell membrane 110 can include, but is not limited to the membrane of bone cells, or any other desired target cell. The cell receptor 105 can include, but is not limited to, the insulin-like growth factor-I (IGF-I) or the Transforming Growth Factor Beta (TGFb) receptor. The cell receptor 105 is typically a protein compound composed of multiple subunits. The subunits include extracellular subunit 105a which is outside of the cell membrane 110, and an intracellular subunit 105c which is inside the cell membrane 110.

Referring now to FIG. 2, there is illustrated a block diagram of a cellular environment. The cellular environment includes any number of cells 205 and extracellular fluid 210. The cell receptors 105 spanning the cell 205 communicate events in the cell's 205 environment with appropriate intracellular machinery 215, such as cell nucleii. Specific events are communicated to, and detected by the cell receptors 105 by means of ligands 220.

Ligands 220 are typically composed of proteins and travel through the intracellular fluid 210 seeking to bind with the cell receptors 105 of cells 205. When the ligand 220 binds with a cell receptor 105, the cell receptor 105 generates a signal 225 which is delivered to the appropriate intracellular machinery 215 inside the cell 205. The signal causes the intracellular machinery 215 to perform certain specific actions. A cell receptor 105 that is bonded to ligand 220 is considered to be in an active state, while a cell receptor 105 which has not bonded to a ligand 220 is said to be in an inactive state.

Osteoporosis is a disease characterized by a decrease in bone mass which leads to spontaneous bone fractures or a bone fracture occurring due to an impact that under normal conditions would not produce a bone fracture. The goal for treating osteoporosis is to build bone strength to a level sufficient to withstand normal loading conditions without failure.

A general paradigm in biology is that mature, fully differentiated cells do not divide. Therefore, to increase the number of bone producing, fully differentiated bone cells it is necessary to first increase the number of pre-osteoblast cells and then induce their maturation into fully differentiated bone cells. The IGF-I ligand 220 is a naturally occurring substance in the body which binds with the IGF-I receptor 105 and causes a signal 225 to be generated instructing the intracellular machinery 215 to divide pre-osteoblast cells 205. The TGFb ligand 220 is a naturally occurring substance in the body which binds with the TGFb receptor 105 and causes a signal 225 to be generated instructing the intracellular machinery 215 to differentiate the cell 205 into a bone cell. However, the same foregoing biological activity will result if alternative means of activating the cell receptors 105 is achieved.

Figures 3, 4:
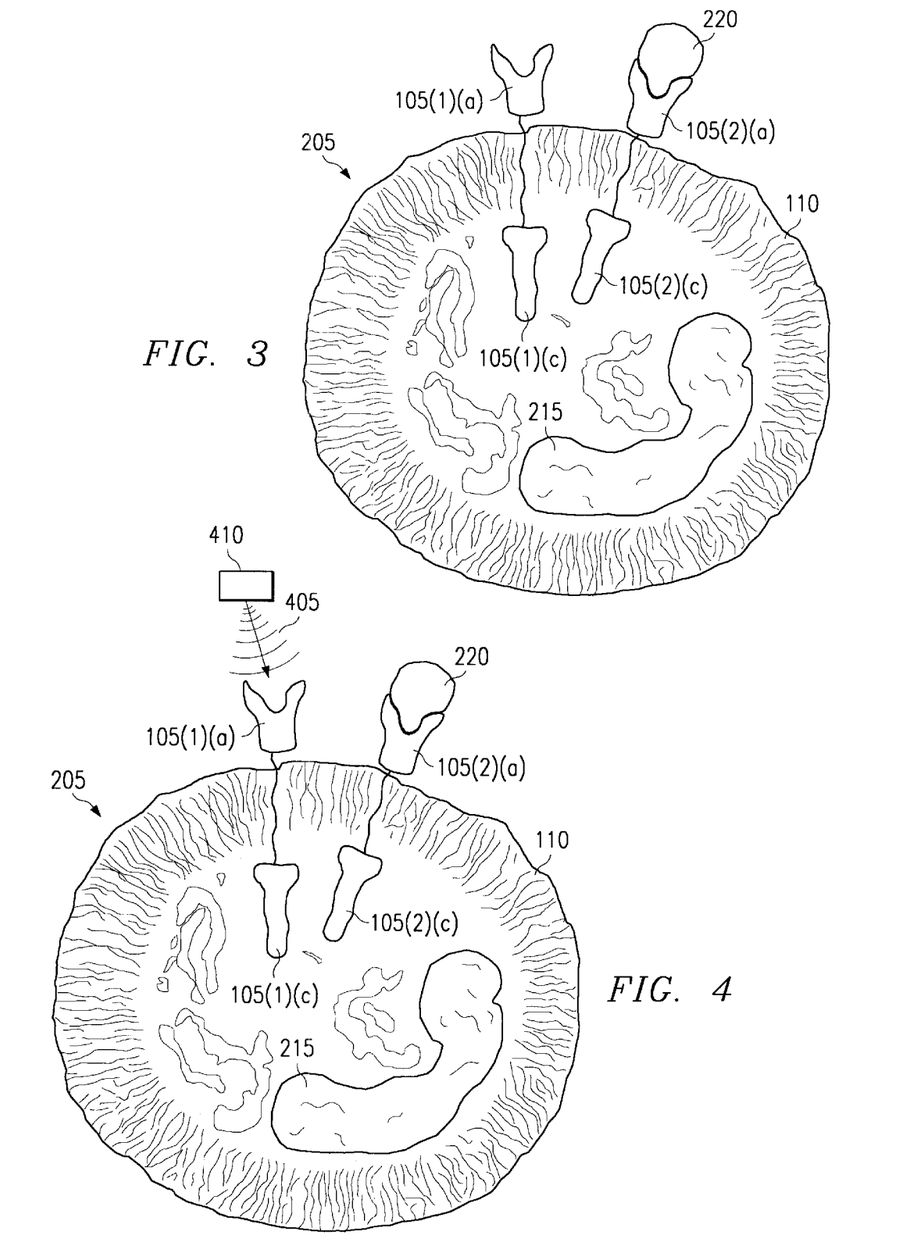
FIG. 3 is a block diagram of an inactive cell receptor and a cell receptor activated by a ligand.
FIG. 4 is a block diagram of cell receptor activity induced in accordance with the principals of the present invention.

Referring now to FIG. 3, there is illustrated a block diagram of an inactive (ell receptor 105(1) and an activated cell receptor 105(2) activated by ligand 220. The intracellular subunit 105(1)(c) and the extracellular subunit 105(1)(a) of the inactive cell receptor 105(1) vibrate in specific relationship to each other. When a ligand 220 binds and activates the cell receptor 105(2), mass is added to the extracellular subunit 105(2)(a). This added mass changes the manner in which the intracellular subunit 105(2)(c) and the extracellular subunit 105(2)(a) vibrate with respect to each other.

The foregoing change in the manner in which the intracellular subunit 105(2)(c) and the extracellular subunit 105(2)(a) vibrate with respect to each other is detected or sensed by the intracellular machinery 215 resulting in the biological effect of the activated cell receptor 105(2). If the manner in which the intracellular subunit 105(1)(c) and the extracellular subunit 105(1)(a) vibrate is changed by an external source to the manner in which the intracellular subunit 105(2)(c) and the extracellular subunit 105(2)(a) vibrate, the biological effect of an activated cell receptor 105(2) will result.

Referring now to FIG. 4, there is illustrated a block diagram of cell receptor activity induced in accordance with the principals of the present invention. To stimulate cell receptor 105 activity, such as cell growth or differentiation, a transmitter 402 for generating an electromagnetic field 405 with a predetermined frequency component to interact with specific cells 205 targeted for cell receptor 105 activity. The electromagnetic field 405 is also referred to as a magnetic field. The term electromagnetic field shall be construed to include both electromagnetic fields and magnetic fields. The electromagnetic field 405 causes the intracellular subunit 105(1)(c) and the extracellular subunit 105(1)(a) to vibrate in a manner simulating the vibrations of the intracellular subunit 105(2)(c) and the extracellular subunit 105(2)(a) of an activated cell receptor 105(2). The vibrations are detected by intracellular machinery 215 resulting in the same biological activity as with the activated cell receptor 105(2).

Figure 5:
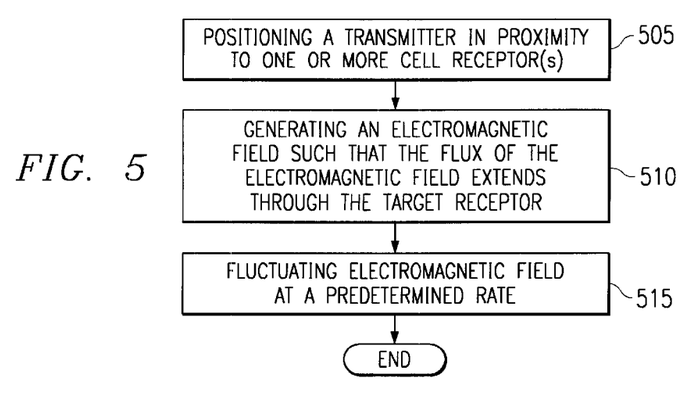
FIG. 5 is a flow chart describing steps of an exemplary method for activating a cell receptor.

Referring now to FIG. 5, there is illustrated a flow chart describing steps off an exemplary method for activating a cell receptor. At step 505, a transmitter 402 is positioned in proximity to one or more target cell receptors 105. An electromagnetic field 405 is generated at step 510, such that the flux of the electromagnetic field extends through the target cell receptors 105. At step 515, the electromagnetic field 405 is fluctuated at a predetermined rate.

Figure 6A:
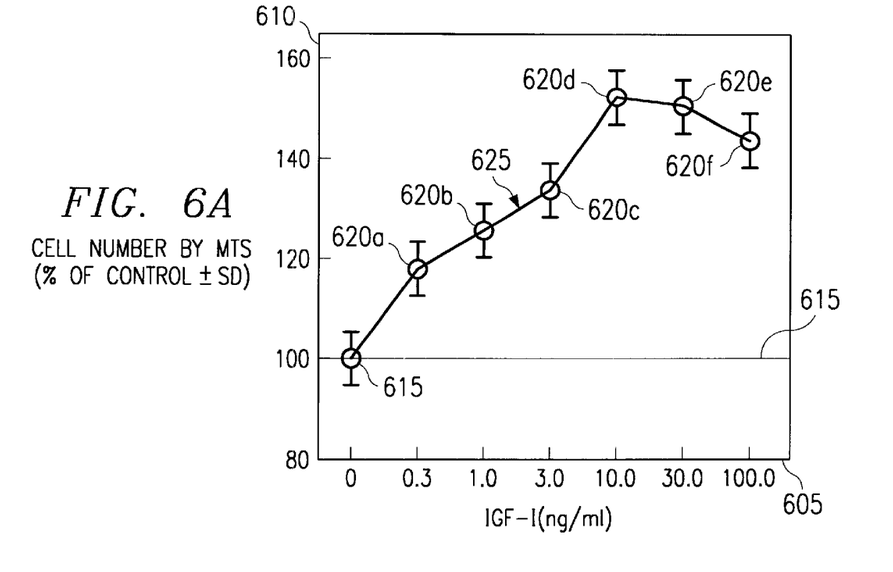
FIG. 6A is a graph of results of a test performed on MG-63 osteosarcoma (MG-63) cell lines.

Referring now to FIG. 6A, there is illustrated a graph of results of a test performed on colonies of the MG-63 osteosarcoma (MG-63 ) cell line known by those skilled in the art for their ability to grow indefinitely and for their sensitivity to the IGF-I ligand. The horizontal axis 605 measures the concentrations of various solutions of IGF-I ligands which were used to treat the MG-63 cell line colonies of equal cell count. The vertical axis 610 measures the MG-63 cell count of each colony as a percentage of the cell count of a control group, represented by a plot 615 at 0 on the horizontal axis 605 and 100% on the vertical axis 610. The cell count of each MG-63 cell line colony twenty-four hours after the treatment as a percentage of the cell count of the control group is represented by plots 620 connected to form curve 625. The cell count results, plots 620, establish that the MG-63 cells proliferate when treated with the IFG-I ligand. A 150% peak 620d is achieved with a 10 nanogram/millileter IGF-I ligand solution.

Figure 6B:
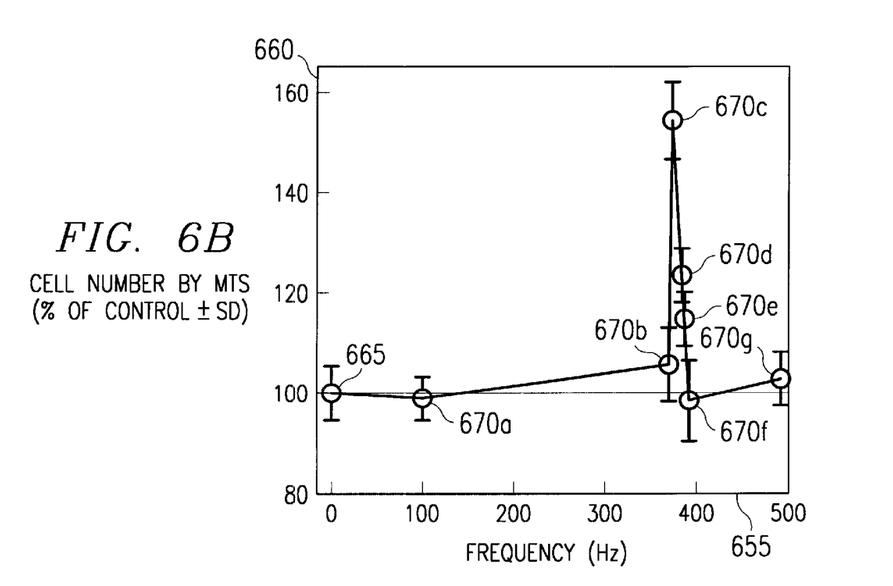
FIG. 6B is a graph of results of another test performed on MG-63 cell lines.

Referring now to FIG. 6B, there is illustrated a graph of results of another test performed on colonies of the MG-63 cell line. The horizontal axis 655 measures the rate of fluctuation of an electromagnetic field applied to the MG-63 cell line colonies of equal cell count. The vertical axis 660 measures the cell count of each MG-63 cell line colony as a percentage of the cell count of a control group, represented by a plot 665 at 0 on the horizontal axis 655 and 100% on the vertical axis 660. The cell count of each MG-63 cell line colony twenty-four hours after the treatment as a percentage of the cell count of the control group is represented by plots 670 connected to form curve 675. The cell count results, plots 670, suggest no statistically significant effect for any rate of fluctuation below 375 Hz and any rate of fluctuation exceeding 385 Hz. However, the cell count of the MG-63 cell line colonies which were exposed to electromagnetic fields which fluctuated at rates between 375 Hz to 385 Hz, represented by plots 670c, 670d, and 670e rose sharply, with highest cell count achieved at a fluctuation rate of 379 Hz. Additionally, the peak cell count of 150% achieved at a fluctuation rate of 379 Hz, represented by plot 670c, mimics the peak cell count, plot 620d, achieved with the IGF-I ligand solution treatment.

Accordingly, IGF-I receptors 105 can be activated, thereby stimulating the proliferation of MG-63 cells 205 using the method steps illustrated in FIG. 5, wherein the electromagnetic field is fluctuated at a rate of approximately 379 Hz, or fluctuated at a rate between 375 Hz and 385 Hz, during step 515.

Figure 7A:
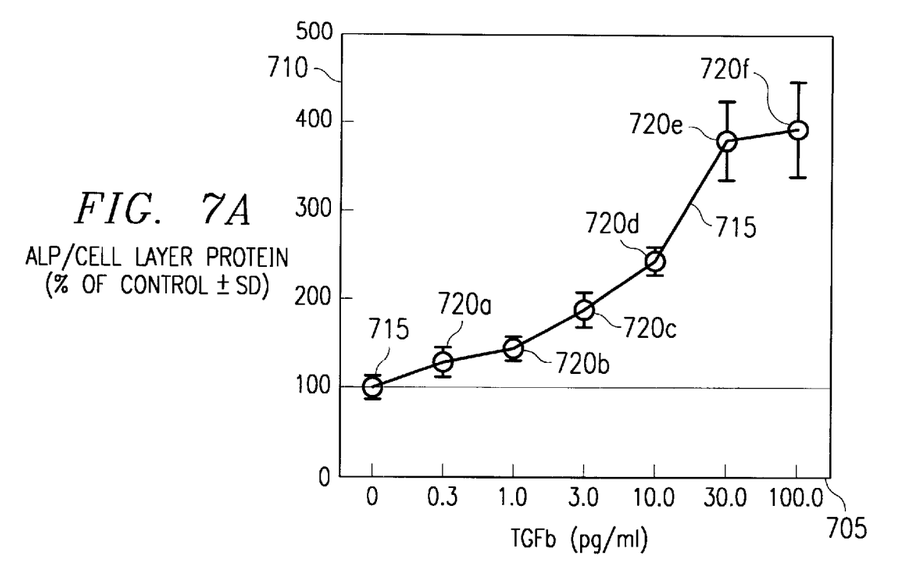
FIG. 7A is a graph of results of another test performed on MG-63 cell lines.

Referring now to FIG. 7A, there is illustrated a graph of results of another test performed on MG-63 cell line colonies. The horizontal axis 705 measures the concentrations of various solutions of TGFb ligands which were used to treat the MG-63 cell line colonies of equal Alkaline Phosphatase (ALP) activity. Those skilled in the art will recognize that AILP activity is commonly used to measure bone cell differentiation. The vertical axis 710 measures the ALP activity of each MG-63 cell line colony as a percentage of the ALP activity of a control group, represented by a plot 715 at 0 on the horizontal axis 705 and 100% on the vertical axis 710. The ALP activity of each MG-63 cell line colony seventy-two hours after the treatment as a percentage of the cell count of the control group is represented by plots 720 connected to form curve 725. The ALP activity results, plots 720, establish that ALP activity is increased, and therefore bone cell differentiation, of the MG-63 cells when treated with the TGFb ligand solution, with a 375% plateau 720e, 720f achieved by a TGFb solutions exceeding 30 picograms/millileter concentration.

Figure 7B:
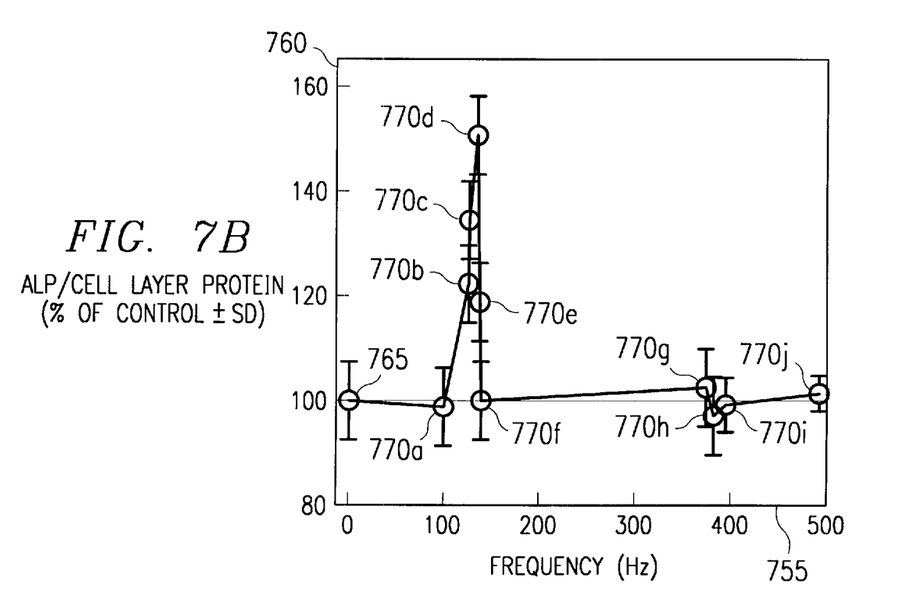
FIG. 7B is a graph of results of another test performed on MG-63 cell lines.

Referring now to FIG. 7B, there is illustrated a graph of results of another test performed on MG-63 cell line colonies. The horizontal axis 755 measures the rate of fluctuation of an electromagnetic field applied to the MG-63 cell line colonies of equal ALP activity. The vertical axis 760 measures the ALP activity of each MG-63 cell line colony as a percentage of the ALP activity of a control group, represented by a plot 765 at 0 on the horizontal axis 755 and 100% on the vertical axis 760. The ALP activity of each MC-63 cell line seventy-two hours after the treatment as a percentage of the ALP activity of the control group is represented by plots 770 connected to form curve 775. The ALP activity results, plots 770, suggest no statistically significant effect for any rate of fluctuation below 130 Hz and any rate of fluctuation exceeding 140 Hz. However, the ALP activity, and therefore cell differentiation, of the MG-63 cell line colonies which were exposed to electromagnetic fields which fluctuated at rates between 130 Hz to 140 Hz, represented by plots 770b, 770c, 770d, and 770e rose sharply, with highest ALP activity/cell differentiation rate of 150% achieved at a fluctuation rate of 133 Hz.

Accordingly, TGFb receptors 105 can be activated, thereby stimulating the differentiation of MG-63 cells 205 using the method steps illustrated in FIG. 5, wherein the electromagnetic field is fluctuated at a rate of approximately 133 Hz, or fluctuated at a rate between 130 Hz and 140 Hz, during step 515. Additionally, no statistically significant activity occurred when the electromagnetic field was fluctuated at rates between 375 Hz to 385 Hz, represented by plots 770g, 770h, and 770i. The foregoing leads to an important conclusion that fluctuating the electromagnetic field at a predetermined rate specifically activates only certain receptors. Therefore, the method steps of FIG. 5 can be applied to large number of cell receptors (as during a non-invasive medical procedure on a living osteoporosis patient) but only stimulates cell receptor activity or activities in certain desired target cells.

Figure 8:
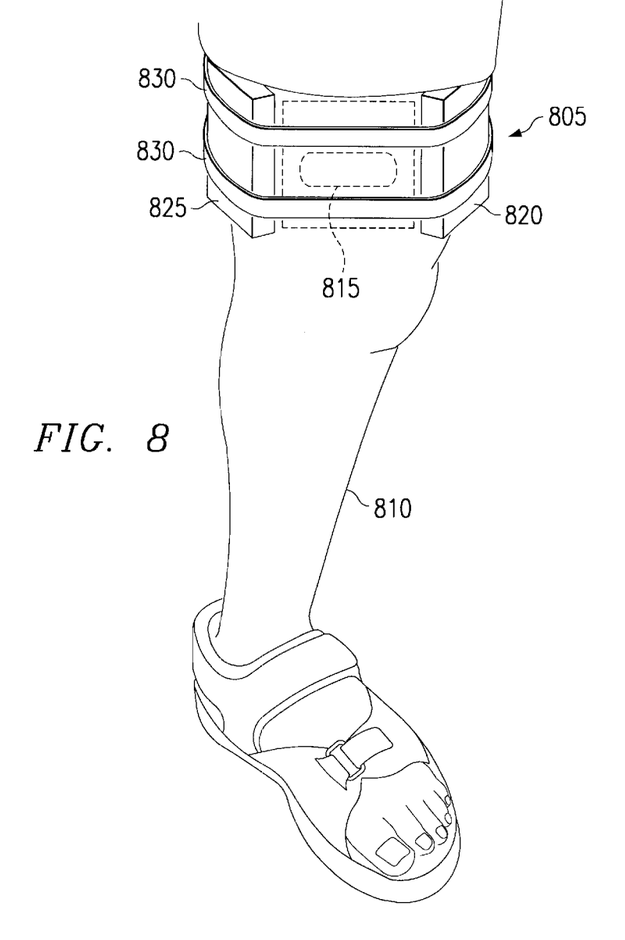
FIG. 8 is a block diagram of a biological receptor activating device positioned onto a limb of a patient fore activating biological receptors.

Referring now to FIG. 8, there is illustrated a block diagram of a cell receptor activating device 805 for activating cell receptors, positioned onto a limb 810 of a patient. The area to b)e treated (treatment area) 815 may be on the surface of the limb 810 or within the limb 810 and contains the biological receptors to be activated. The cell receptor activating device 805 includes two transmitter heads 820, 825 capable of generating an electromagnetic field. The transmitter heads 820, and 825 are positioned and secured in proximity to the treatment area 815 containing the target receptors such that the flux of the electromagnetic field extends through the target receptors by means of bands 830, which can comprise a strap, a belt, a rope, or a tie. The transmitter heads 320, and 825 can also be positioned and secured in proximity to the treatment area 815 by a clamp, an adhesive, or via integration into a cast.

Figure 9:
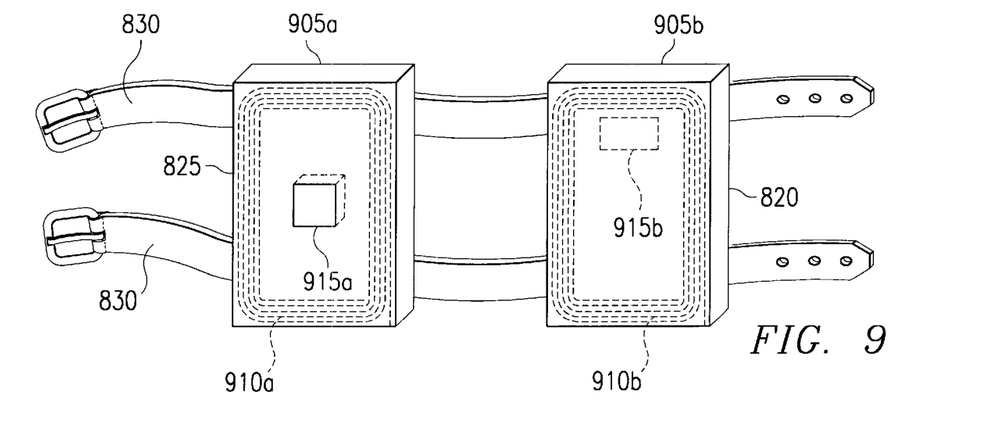
FIG. 9 is a block diagram of transmitter heads forming a portion of the biological receptor activating device shown in FIG. 8.

Referring now to FIG. 9, there is illustrated a block diagram of transmitter heads 820, 825. Each transmitter head 820, 825 includes a housing 905a, 905b of a non-magnetic material, such as plastic which encloses a field coil 910a, 910b. Each transmitter head 820, 825 also includes an alternating (AC) current source 915a, 915b electrically connected to each field coil 910a, 910b. The AC current source 915a, 915b, is capable of generating an AC current with a predetermined rate of fluctuation, which flows through the field coils 910a, 910b. The predetermined rate of fluctuation can either be user settable, or set in accordance with manufacturing specifications. When the AC current flows through the field coils 910a, 910b, an electromagnetic field is generated. Additionally, the magnitude of the electromagnetic field is proportional to the instantaneous magnitude of the AC current. Therefore, the electromagnetic field fluctuates at the predetermined rate of fluctuation of the AC current.

Although preferred embodiments of the present inventions have illustrated in the accompanying Drawings and described in the foregoing Detailed Description, it will be understood that the inventions are not limited to the embodiments disclosed, but are capable of numerous rearrangements, modifications and substitutions without departing from the spirit of the invention as set forth and defined by the following claims and equivalents thereof.

What is claimed is:

1. A method for activating an insulin-like growth factor-I receptor, the method comprising:

positioning a transmitter in proximity to the insulin-like growth factor-I receptor;

generating an electromagnetic field having a rate of fluctuation of about 379 Hz to activate the insulin-like growth factor-I receptor such that the flux of the electromagnetic field extends through the insulin-like growth factor-I receptor.

2. A device for activating an insulin-like growth factor-I receptor, the device comprising:

a transmitter for generating an electromagnetic field having a rate of fluctuation between 375 Hz and 385 Hz to activate the insulin-like growth factor-I receptor; and a positioning apparatus operable to position the transmitter such that the flux of the magnetic field will extend through the insulin-like growth factor-I receptor.

3. The device of claim 2, wherein the transmitter further comprises a coil.

4. The device of claim 2, wherein the positioning apparatus is selected from a group consisting of a cast, a clamp, an orthopedic device, an orthopedic support, a strap, support, an adhesive, a belt, a rope, and a tie.

5. A method for activating a transforming growth factor beta receptor, the method comprising:

positioning a transmitter in proximity to the transforming growth beta receptor;

generating an electromagnetic field having a rate of fluctuation of about 133 Hz to activate the transforming growth beta receptor such that the flux of the electromagnetic field extends through the transforming growth beta receptor.

6. A device for activating a transforming growth factor beta receptor, said device comprising:

a transmitter for generating an electromagnetic field having a rate of fluctuation between 130 Hz and 140 Hz to activate the transforming growth factor beta receptor; and a positioning apparatus operable to position the transmitter such that the flux of the magnetic field will extend through the transforming growth factor beta receptor.

7. The device of claim 5, wherein the transmitter further comprises a coil.

8. The device of claim 5, wherein the positioning apparatus is selected from a group consisting of a cast, a clamp, an orthopedic device, an orthopedic support, a strap, a support, an adhesive, a rope, and a tie.

* * * * *

UNITED STATES PATENT AND TRADEMARK OFFICE
CERTIFICATE OF CORRECTION

PATENT NO. : 6,364,824 B1 Page 1 of 1
DATED : April 2, 2002
INVENTOR(S) : Fitzsimmons, Robert J.

It is certified that error appears in the above-identified patent and that said Letters Patent is hereby corrected as shown below:

<u>Column 1,</u>
Line 24, delete ":";

<u>Column 4,</u>
Line 18, delete "(ell" and insert in lieu thereof -- cell --;

<u>Column 6,</u>
Line 47, delete "320" and insert in lieu thereof -- 820 --.

Signed and Sealed this

Seventeenth Day of September, 2002

*Attest:*

JAMES E. ROGAN
*Attesting Officer* *Director of the United States Patent and Trademark Office*